(12) United States Patent
Yasunaga et al.

(10) Patent No.: US 8,947,650 B2
(45) Date of Patent: Feb. 3, 2015

(54) REFRACTIVE INDEX MEASURING DEVICE AND REFRACTIVE INDEX MEASURING METHOD

(75) Inventors: Hirotoshi Yasunaga, Osaka (JP); Koji Yamabuchi, Osaka (JP); Takeshi Ishida, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 120 days.

(21) Appl. No.: 13/823,144

(22) PCT Filed: Sep. 9, 2011

(86) PCT No.: PCT/JP2011/070549
§ 371 (c)(1),
(2), (4) Date: Mar. 14, 2013

(87) PCT Pub. No.: WO2012/036075
PCT Pub. Date: Mar. 22, 2012

(65) Prior Publication Data
US 2013/0182245 A1    Jul. 18, 2013

(30) Foreign Application Priority Data

Sep. 16, 2010    (JP) ................. 2010-208125

(51) Int. Cl.
*G01N 21/41* (2006.01)
*G01N 21/43* (2006.01)

(52) U.S. Cl.
CPC ............. *G01N 21/41* (2013.01); *G01N 21/43* (2013.01)
USPC .......................... 356/128; 356/135

(58) Field of Classification Search
CPC .......... G01N 21/553; G01N 33/54373; G01N 21/45; G01N 21/43; G01N 33/54393; G01N 21/05; G01N 21/554; G01N 21/00; G01N 21/211; G01N 21/23; G01N 21/41; G01N 21/4133; G01N 21/8422; G01N 33/544
See application file for complete search history.

(56) References Cited

U.S. PATENT DOCUMENTS

| | | | | |
|---|---|---|---|---|
| 4,692,024 | A | * | 9/1987 | Bloss ............................ 356/135 |
| 8,379,228 | B1 | * | 2/2013 | Streater ........................ 356/630 |
| 2009/0021727 | A1 | * | 1/2009 | Sepulveda Martinez et al. ............................. 356/128 |

FOREIGN PATENT DOCUMENTS

| | | |
|---|---|---|
| JP | 52-102769 U | 8/1977 |
| JP | 52-135757 A | 11/1977 |
| JP | 63-051260 B2 | 10/1988 |
| JP | 06-288902 A | 10/1994 |
| JP | 09-054039 A | 2/1997 |
| JP | 2009-162561 A | 7/2009 |

OTHER PUBLICATIONS

Official Communication issued in International Patent Application No. PCT/JP2011/070549, mailed on Oct. 18, 2011.

* cited by examiner

*Primary Examiner* — Michael P Stafira
(74) *Attorney, Agent, or Firm* — Keating & Bennett, LLP

(57) ABSTRACT

In a refractive index measuring device (1) for measuring a refractive index of a solid sample (S), the solid sample (S) is closely attached to a prism (3) having a predetermined refractive index with a refractive index liquid (4) having a predetermined refractive index interposed therebetween. A scaled angle (light receiving member) (6) having a light receiving surface (6a) that receives first reflected light (R1), which is a part of light from a light source (2) and which is reflected by the prism (3), is provided. When the prism (3) is rotationally driven by a rotary table (rotational drive unit) (5) and an intensity of second reflected light (R2) detected by a detector (7) becomes lower than a predetermined value, the refractive index of the solid sample (S) is measured by using a position of the first reflected light (R1) on the light receiving surface (6a) of the scaled angle (6).

7 Claims, 10 Drawing Sheets

(a)

(b)

REFRACTIVE INDEX MEASURING DEVICE AND REFRACTIVE INDEX MEASURING METHOD

TECHNICAL FIELD

The present invention relates to a refractive index measuring device and a refractive index measuring method for measuring a refractive index of a material, in particular, a solid sample such as an optical element.

BACKGROUND ART

Recently, liquid crystal display devices, for example, have been widely used in liquid crystal television sets, monitors, mobile phones, etc., as flat panel displays that are thinner and lighter than conventional cathode-ray tubes. Such a liquid crystal display device includes an illuminating device (backlight) that emits light and a liquid crystal panel that displays a desired image by functioning as a shutter that blocks the light from a light source included in the illuminating device.

The above-described illuminating device generally includes optical elements including, for example, an optical sheet, such as a prism sheet, and an optical waveguide to improve the utilization efficiency of light from the light source, to irradiate the liquid crystal panel with planar illuminating light, or to increase the brightness of the illuminating light.

To evaluate the optical characteristics of such an optical element, it is very important to determine a refractive index of the optical element. This is because the higher the determination accuracy of the refractive index of the optical element, the easier an illuminating device having desired optical (luminous) characteristics can be produced in the case where the optical element is used in the above-described illuminating device.

As a refractive index measuring method according to the related art, a method of measuring a refractive index of a test subject (solid sample) by a total reflection method using a prism has been proposed in, for example, PTL 1 below. More specifically, in this refractive index measuring method according to the related art, the relationship between an incident angle of light incident on a reflection surface of a prism and the intensity of light reflected by the reflection surface is determined in each of a state in which a test subject is in contact with the reflection surface and a state in which only air is in contact with the reflection surface. In this refractive index measuring method according to the related art, the relationship between the incident angle and the reflected light intensity in the state in which the test subject is in contact with the reflection surface is normalized by using the relationship between the incident angle and the reflected light intensity in the state in which only air is in contact with the reflection surface. Then, the refractive index of the test subject is measured on the basis of the normalized relationship between the incident angle and the reflected light intensity.

CITATION LIST

Patent Literature

PTL 1: Japanese Unexamined Patent Application Publication No. 2009-162561

SUMMARY OF INVENTION

Technical Problem

However, the above-described refractive index measuring method according to the related art has a problem in that it is difficult to increase the accuracy of measurement of the refractive index of the test subject (solid sample).

More specifically, in the above-described refractive index measuring method according to the related art, a light-emitting optical system that emits light toward the reflection surface of the prism is configured to be rotatable around the center of the reflection surface of the prism so that the incident angle of the light on the reflection surface of the prism can be changed gradually. According to the refractive index measuring method of the related art, the refractive index of the test subject is obtained by determining the relationship between the incident angle and the reflected light intensity in each of the above-described two states while the light-emitting optical system is rotated so as to vary the incident angle of the light on the reflection surface of the prism.

In the refractive index measuring method according to the related art, as described above, the incident angle of the light on the reflection surface of the prism is varied by rotating the light-emitting optical system. In other words, in the refractive index measuring method according to the related art, the accuracy of measurement of the refractive index of the test subject depends on the rotational angle, and the refractive index largely changes when the rotational angle is changed by 1°. Because of the above and because there is a limit to the accuracy in controlling the rotational angle, it is difficult to increase the accuracy of measurement of the refractive index of the test subject (solid sample) in the above-described refractive index measuring method according to the related art.

In light of the above-described problems, an object of the present invention is to provide a refractive index measuring device and a refractive index measuring method with which the accuracy of measurement of a refractive index of a solid sample can be increased.

Solution to Problem

To achieve the above-described object, a refractive index measuring device according to the present invention is a refractive index measuring device for measuring a refractive index of a solid sample, the refractive index measuring device including a light source; a prism having a predetermined refractive index and including a first surface on which light from the light source is incident and a second surface which emits light that has passed through the first surface toward the solid sample; a rotational drive unit that rotationally drives the prism; a refractive index liquid that has a predetermined refractive index and with which the solid sample is closely attached to the second surface of the prism; a light receiving member having a light receiving surface that receives first reflected light, which is a part of the light from the light source and which is reflected by the first surface of the prism; and a detector that receives second reflected light, which is a part of the light from the second surface of the prism and which is reflected by a surface of the solid sample that faces the refractive index liquid, and detects an intensity of the received second reflected light. When the prism is rotationally driven by the rotational drive unit and the intensity of the second reflected light detected by the detector becomes lower than a predetermined value, the refractive index of the solid sample is measured by using a position of the first reflected light on the light receiving surface of the light receiving member.

In the refractive index measuring device having the above-described structure, when the prism is rotationally driven by the rotational drive unit and the intensity of the second reflected light detected by the detector becomes lower than a predetermined value, the refractive index of the solid sample is measured by using the position of the first reflected light on the light receiving surface of the light receiving member. Accordingly, unlike the above-described example of the related art, the accuracy of measurement of the refractive index of the solid sample can be increased by increasing the distance between the prism and the light receiving surface of the light receiving member.

More specifically, in the above-described refractive index measuring device, it can be determined that the incident angle of the light on the solid sample has become equal to the critical angle when the intensity of the second reflected light has become lower than the predetermined value. The incident angle of the light from the light source on the first surface at the time when the incident angle of the light on the solid sample has become equal to the critical angle can be determined from the position of the first reflected light on the light receiving surface of the light receiving member. The refractive index of the solid sample can be determined by using the incident angle of the light on the first surface. The position of the first reflected light on the light receiving surface of the light receiving member depends on the rotational angle of the prism. A difference in the position of the first reflected light on the light receiving surface of the light receiving member, the difference corresponding to a difference in the rotational angle of the prism, increases as the distance between the prism and the light receiving surface of the light receiving member increases. Therefore, when the incident angle of the light on the first surface is calculated on the basis of the position of the first reflected light, the incident angle of the light on the first surface can be determined with an accuracy that cannot be achieved by an adjustment of the rotational angle of the prism. As a result, the refractive index of the solid sample can be very accurately determined.

In the above-described refractive index measuring device, preferably, the light source and the prism are arranged so that the first reflected light is reflected toward the light receiving surface of the light receiving member by the first surface of the prism at a center of rotation of the prism, and the refractive index of the solid sample is measured by using a distance between the center of rotation and an orthogonal position, which is a position where a perpendicular dropped from the center of rotation to the light receiving surface of the light receiving member reaches the light receiving surface, and a distance between the orthogonal position on the light receiving surface and a position of the first reflected light on the light receiving surface of the light receiving member.

In this case, the refractive index of the solid sample can be easily determined.

In addition, in the above-described refractive index measuring device, preferably, scale marks are provided on the light receiving surface of the light receiving member, the scale marks including a scale mark indicating a standard position of the first reflected light in the case where the solid sample has a standard refractive index and scale marks which have predetermined intervals therebetween and which indicate displacements from the standard position.

In this case, the refractive index of the solid sample can be more easily determined.

In addition, in the above-described refractive index measuring device, preferably, the scale marks provided on the light receiving surface of the light receiving member correspond to refractive indices within an allowable refractive index range of the solid sample.

In this case, it can be instantly determined whether or not the solid sample has an acceptable refractive index and the process of inspecting the solid sample can be simplified.

In addition, in the above-described refractive index measuring device, preferably, the prism has a shape of a regular triangular prism.

In this case, the refractive index of the solid sample can be easily determined compared to the case in which prisms having other shapes are used.

A refractive index measuring method according to the present invention is a refractive index measuring method for measuring a refractive index of a solid sample, the refractive index measuring method including a solid-sample attaching step of closely attaching the solid sample to a second surface of a prism with a refractive index liquid having a predetermined refractive index interposed therebetween, the prism having a predetermined refractive index and including a first surface on which light from a light source is incident and the second surface which emits light that has passed through the first surface; a light incidence step of receiving first reflected light with a light receiving surface of a light receiving member, the first reflected light being reflected by the first surface of the prism when the light from the light source is incident on the first surface, and receiving second reflected light with a detector, the second reflected light being a part of the light from the second surface of the prism and being reflected by a surface of the solid sample that faces the refractive index liquid; and a refractive index detecting step of rotating the prism while the solid sample is attached to the prism, determining whether or not an intensity of the second reflected light detected by the detector is lower than a predetermined value, and determining the refractive index of the solid sample by using a position of the first reflected light on the light receiving surface of the light receiving member when it is determined that the intensity has become lower than the predetermined value.

According to the above-described refractive index measuring method, in the refractive index detecting step, which is performed after the solid-sample attaching step and the light incidence step, the prism is rotated while the solid sample is attached to the prism, and it is determined whether or not the intensity of the second reflected light detected by the detector is lower than the predetermined value. When it is determined that the intensity has become lower than the predetermined value, the refractive index of the solid sample is detected by using the position of the first reflected light on the light receiving surface of the light receiving member. Accordingly, in the refractive index detecting step, the accuracy of measurement of the refractive index of the solid sample can be increased by increasing the distance between the prism and the light receiving surface of the light receiving member.

In the above-described refractive index measuring method, preferably, in light incidence step, the light from the light source is incident on the first surface of the prism so that the first reflected light is reflected toward the light receiving surface of the light receiving member by the first surface of the prism at a center of rotation of the prism. In addition, preferably, in the refractive index detecting step, the refractive index of the solid sample is measured by using a distance between the center of rotation and an orthogonal position, which is a position where a perpendicular dropped from the center of rotation to the light receiving surface of the light receiving member reaches the light receiving surface, and a distance between the orthogonal position on the light receiving surface and a position of the first reflected light on the light receiving surface of the light receiving member.

In this case, the refractive index of the solid sample can be easily determined.

In addition, in the above-described refractive index measuring method, preferably, in the refractive index detecting step, the refractive index of the solid sample is measured by using scale marks provided on the light receiving surface of the light receiving member.

In this case, the refractive index of the solid sample can be more easily determined.

In addition, in the above-described refractive index measuring method, preferably, in the refractive index detecting step, the scale marks used to measure the refractive index of the solid sample correspond to refractive indices within an allowable refractive index range of the solid sample.

In this case, it can be instantly determined whether or not the solid sample has an acceptable refractive index and the process of inspecting the solid sample can be simplified.

Advantageous Effects of Invention

The present invention provides a refractive index measuring device and a refractive index measuring method with which the accuracy of measurement of a refractive index of a solid sample can be increased.

DESCRIPTION OF EMBODIMENTS

Figure 1:
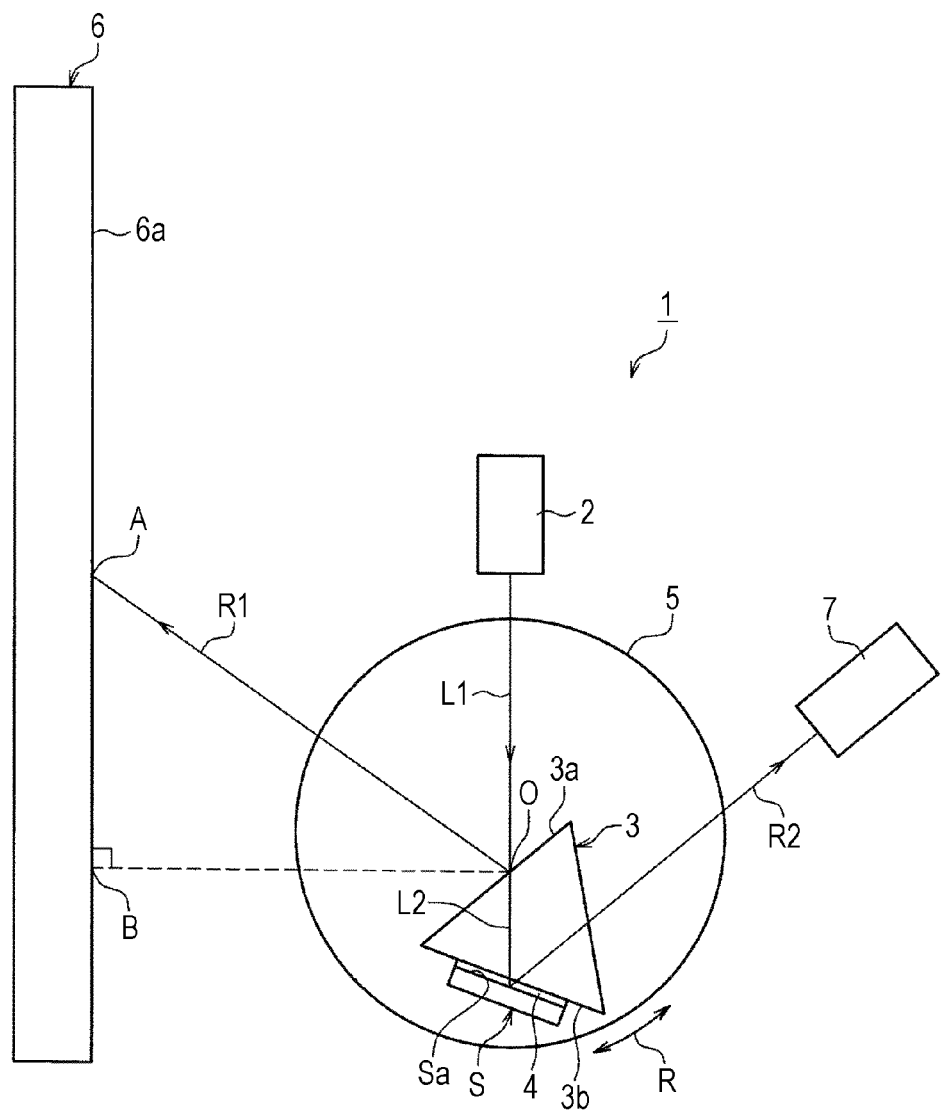
FIG. 1 illustrates the overall structure of a refractive index measuring device according to a first embodiment of the present invention.

Refractive index measuring devices and refractive index measuring methods according to preferred embodiments of the present invention will now be described with reference to the drawings. In the drawings, dimensions of components do not accurately reflect the actual dimensions, ratios between the dimensions, etc., of the components.

First Embodiment

FIG. 1 illustrates the overall structure of a refractive index measuring device according to a first embodiment of the present invention. Referring to the figure, a refractive index measuring device 1 according to the present embodiment includes a light source 2 and a prism 3 which has a predetermined refractive index and to which a solid sample S is attached with a refractive index liquid 4 interposed therebetween. The solid sample S serves as a measurement subject whose refractive index is to be measured. The refractive index measuring device 1 according to the present embodiment also includes a rotary table 5 on which the prism 3 is placed and which serves as a rotational drive unit that rotationally drives the prism 3, a scale 6, and a detector 7. The scale 6 and the detector 7 respectively receive first reflected light R1 and second reflected light R2, which will be described below.

The light source 2 is secured at a predetermined position, and is configured so that incident light L1 is incident on a first surface 3a of the prism 3. The light source 2 emits parallel light, preferably, parallel light having a small area, as the incident light L1. More specifically, a laser source that emits a laser beam or a combination of a light tube or bulb (lamp), a lens, and an aperture, for example, may be used as the light source 2.

In the present embodiment, the light source 2 and the prism 3 are arranged so that the incident light L1 is incident on the first surface 3a of the prism 3 at a center of rotation O of the prism 3 (that is, at the rotation axis of the rotary table 5). In addition, the light source 2 is arranged so that the distance between the light source 2 and the prism 3 is as small as possible. Thus, when the prism 3 is rotationally driven, a displacement of the point at which the incident light L1 is incident on the first surface 3a from the center of rotation O can be made as small as possible.

The prism 3 is formed of, for example, a glass material having a predetermined refractive index, such as 1.779. The prism 3 has the shape of, for example, a regular triangular prism, and includes the first surface 3a on which the light L1 from the light source 2 is incident and a second surface 3b to which the solid sample S is attached with the refractive index liquid 4 and which emits light L2 that has passed through the first surface 3a toward the solid sample S.

The prism 3 is fixed to the rotary table 5, and can be rotated by the rotary table 5 while the solid sample S is attached thereto. The rotary table 5 has a handle (not shown) or a motor (not shown) attached thereto, and is configured to rotationally drive the prism 3 in the directions shown by both-ended arrow R.

The refractive index liquid 4 has a predetermined refractive index, and is used to closely attach the solid sample S to the second surface 3b of the prism 3 without leaving an air layer therebetween. Thus, the solid sample S is closely attached to the second surface 3b with the refractive index liquid 4 interposed therebetween. Therefore, even when a surface of the solid sample S that faces the prism 3 (refractive index liquid 4) is not flat, that is, even when the surface has, for example, an irregular shape, adverse influence of the shape on the measurement of the refractive index of the solid sample S can be reduced and the refractive index can be accurately measured.

The scale 6 constitutes a light receiving member having a light receiving surface 6a that receives the first reflected light R1, which is a part of the light from the light source 2 and which is reflected by the first surface 3a of the prism 3. In the present embodiment, the light source 2 and the scale 6 are arranged so that the light receiving surface 6a is parallel to the incident light L1 that travels from the light source 2 to the prism 3. The light receiving surface 6a of the scale 6 has, for example, a planar shape. The light receiving surface 6a is configured such that the distance between a (light-receiving)

position A of the first reflected light R1 and an orthogonal position B, which is a position where a perpendicular dropped from the center of rotation O of the prism 3 to the light receiving surface 6a reaches the light receiving surface 6a, can be determined. More specifically, the orthogonal position B is set as a reference point, and scale marks indicating the distance from the reference point in a direction parallel to the incident light L1 (vertical direction in the figure) are provided on the light receiving surface 6a, so that the distance between the position A and the orthogonal position B can be determined.

In the refractive index measuring device 1 according to the present embodiment, as described below, the refractive index of the solid sample S is determined by using the distance between the center of rotation O and the orthogonal position B and the distance between the position A of the first reflected light R1 and the orthogonal position B. In addition, in the refractive index measuring device 1 according to the present embodiment, the accuracy of measurement of the refractive index of the solid sample S can be changed by changing the distance between the center of rotation O and the orthogonal position B (this will be described in more detail below).

The detector 7 receives the second reflected light R2, which is a part of the light from the second surface 3b of the prism 3 and which is reflected by a surface Sa of the solid sample S that faces the refractive index liquid 4, and detects the intensity of the received second reflected light R2. A power meter or an illuminometer that is capable of detecting the intensity of the second reflected light R2, for example, is used as the detector 7. In the case where the light emitted from the light source 2 is not single-wavelength light, the detector 7 preferably includes a spectroscope.

In addition to the above-described structure, a mirror may be disposed between the surface Sa of the solid sample S and the detector 7 so that the second reflected light R2 is incident on the detector 7 via the mirror. A mirror may also be disposed on an optical path of the incident light L1 or an optical path of the first reflected light R1.

In the refractive index measuring device 1 according to the present embodiment having the above-described structure, the refractive index of the solid sample S is measured by sequentially performing a solid-sample attaching step, a light incidence step, and a refractive index detecting step, which will be described below. As described in detail below, the refractive index measuring device 1 according to the present embodiment is capable of measuring not only the refractive index of the solid sample S that has a single-layer structure formed of a single material having a certain refractive index, but also a refractive index of each of a plurality of materials of a solid sample that has a multilayer structure formed of materials having different refractive indices.

More specifically, in the solid-sample attaching step, the solid sample S is closely attached to the second surface 3b of the prism 3 with the refractive index liquid 4 having the predetermined refractive index interposed therebetween. The prism 3 has the predetermined refractive index and includes the first surface 3a on which the light from the light source 2 is incident and the second surface 3a which emits light that has passed through the first surface 3a.

In the light incidence step, the first reflected light R1 that is reflected by the first surface 3a of the prism 3 when the incident light L1 from the light source 2 is incident on the first surface 3a is received by the light receiving surface 6a of the scale (light receiving member) 6. The light from the light source 2 is incident on the first surface 3a of the prism 3 so that the first reflected light R1 is reflected toward the light receiving surface 6a of the scale 6 by the first surface 3a of the prism 3 at the center of rotation O of the prism 3, that is, so that the center of rotation O of the prism 3 coincides with the light illumination (incident) point. The incident light L1 from the light source 2 is divided into the first reflected light R1 and the light L2 that enters the prism 3, passes through the prism 3, and is emitted from the second surface 3b toward the refractive index liquid 4 (solid sample S).

In addition, in the light incidence step, the detector 7 receives the second reflected light R2, which is a part of the light from the second surface 3b of the prism 3 and which is reflected by the surface Sa of the solid sample S that faces the refractive index liquid 4 (that is, the interface between the prism 3 and the refractive index liquid 4). Thus, in the light incidence step, the light L2 that has passed through the prism 3 is incident on the surface Sa of the solid sample S that is bonded to the prism 3 with the refractive index liquid 4. When the incident angle on the surface Sa is sufficiently large, all of the incident light is reflected as the second reflected light R2 (total reflection). When the incident angle is smaller than a certain value, a part of the incident light is reflected as the second reflected light R2 and another part of the incident light propagates through the solid sample S. Subsequently, the second reflected light R2 is emitted from the prism 3 and is incident on the detector 7.

Whether the light L2 is totally reflected by the surface Sa or a part thereof propagates through the solid sample S depends on whether or not the incident angle on the solid sample S is greater than a critical angle. More specifically, it depends on the refractive index of the solid sample S and the incident angle on the first surface 3a in the case where the prism 3 having the same refractive index is used. Therefore, in the refractive index detecting step, the refractive index of the solid sample S can be calculated from the Snell's law by rotating the prism 3 to which the solid sample S is bonded and determining the incident angle on the first surface 3a at which the intensity of the second reflected light R2 becomes lower than a predetermined value.

More specifically, in the refractive index detecting step, the prism 3 is rotated by the rotary table 5 while the solid sample S is attached thereto. Then, it is determined whether or not the intensity of the second reflected light R2 detected by the detector 7 is lower than the predetermined value. When it is determined that the intensity has become lower than the predetermined value, the refractive index of the solid sample S is detected by using the position A of the first reflected light R1 on the light receiving surface 6a of the scale 6.

More specifically, the detector 7 detects the intensity of the second reflected light R2 while the prism 3 is being rotated, and a point at which the intensity suddenly changes (suddenly drops) is determined. Since the condition of total reflection is not satisfied at this point, the intensity of the second reflected light R2 drops, for example, from 7,000 lux to 1,500 lux. In this case, the above-described predetermined value may be set to, for example, 4,000 lux so that the point at which the condition of total reflection was no longer satisfied can be reliably determined. When the incident angle on the solid sample S is calculated from the position A of the first reflected light R1 at the time when it is determined that the intensity of the second reflected light R2 has become lower than the predetermined value, the calculated incident angle is equal to the critical angle. The critical angle is determined by the refractive indices of the materials on both sides of the surface Sa of the solid sample S. Therefore, when the refractive index of the refractive index liquid 4 is known, the refractive index of the solid sample S can be determined.

In the refractive index detecting step according to the present embodiment, the refractive index of the solid sample S is measured by using the distance between the center of rotation O and the orthogonal position B, which is a position where a perpendicular dropped from the center of rotation O to the light receiving surface 6a of the scale 6 reaches the light receiving surface 6a, and the distance between the orthogonal position B on the light receiving surface 6a and the position A of the first reflected light R1 on the light receiving surface 6a of the scale 6. In other words, in the refractive index detecting step, the refractive index of the solid sample S is detected by determining the above-described critical angle by using a right triangle OAB illustrated in FIG. 1.

In the right triangle OAB, an amount of movement of the position A of the first reflected light R1 per unit rotational angle of the prism 3 increases as the distance between the center of rotation O and the orthogonal position B increases. Therefore, in the present embodiment, as the distance between the center of rotation O and the orthogonal position B increases, the rotational angle of the prism 3 per unit distance along the light receiving surface 6a of the scale 6 decreases, and a variation in the calculated refractive index of the solid sample S per unit distance along the light receiving surface 6a also decreases. In other words, in the present embodiment, the accuracy of measurement of the refractive index of the solid sample S can be increased as the distance between the center of rotation O and the orthogonal position B increases.

A refractive index calculating method carried out by the refractive index measuring device 1 according to the present embodiment will now be described in more detail with reference also to FIGS. 2 to 6.

Figure 2:
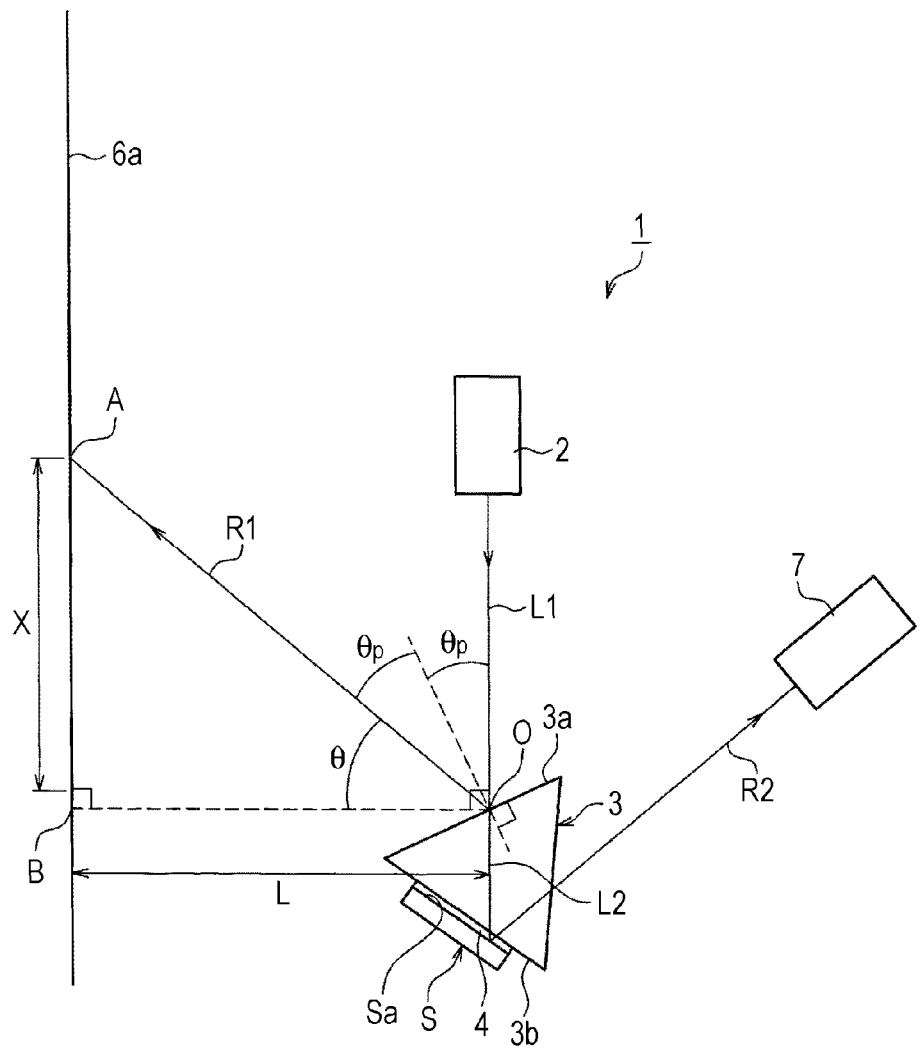
FIG. 2 illustrates a specific example of a refractive index calculating method carried out by the refractive index measuring device.
Figure 3:
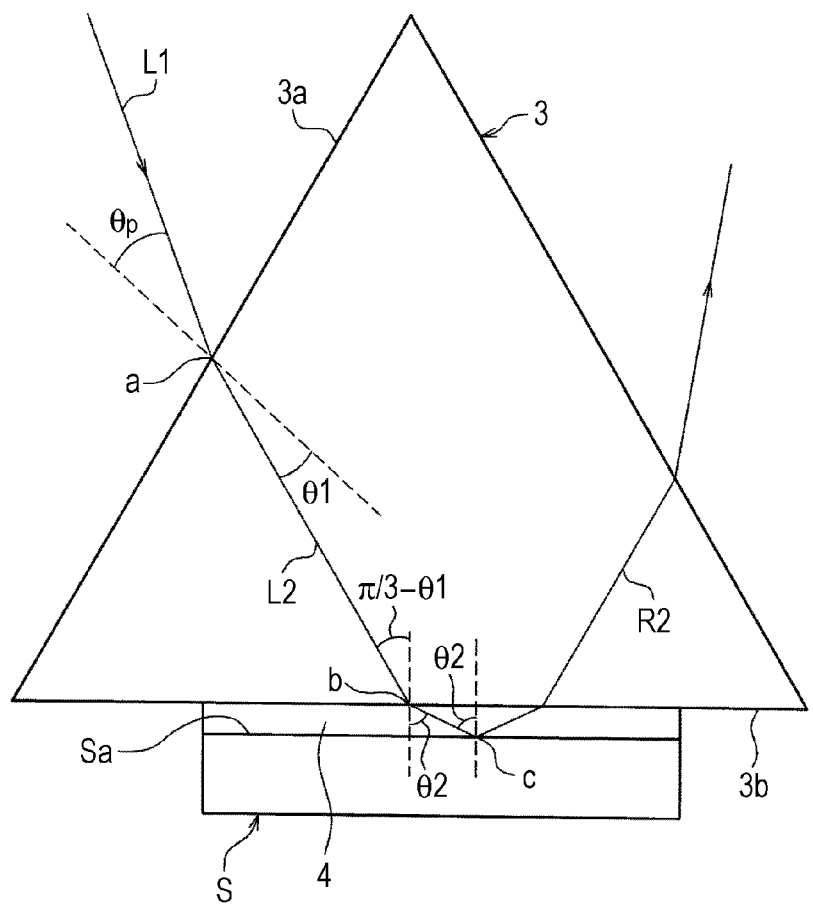
FIG. 3 illustrates a specific example of a refractive index calculating method carried out by the refractive index measuring device in the case where a solid sample has a single-layer structure.
Figure 4:
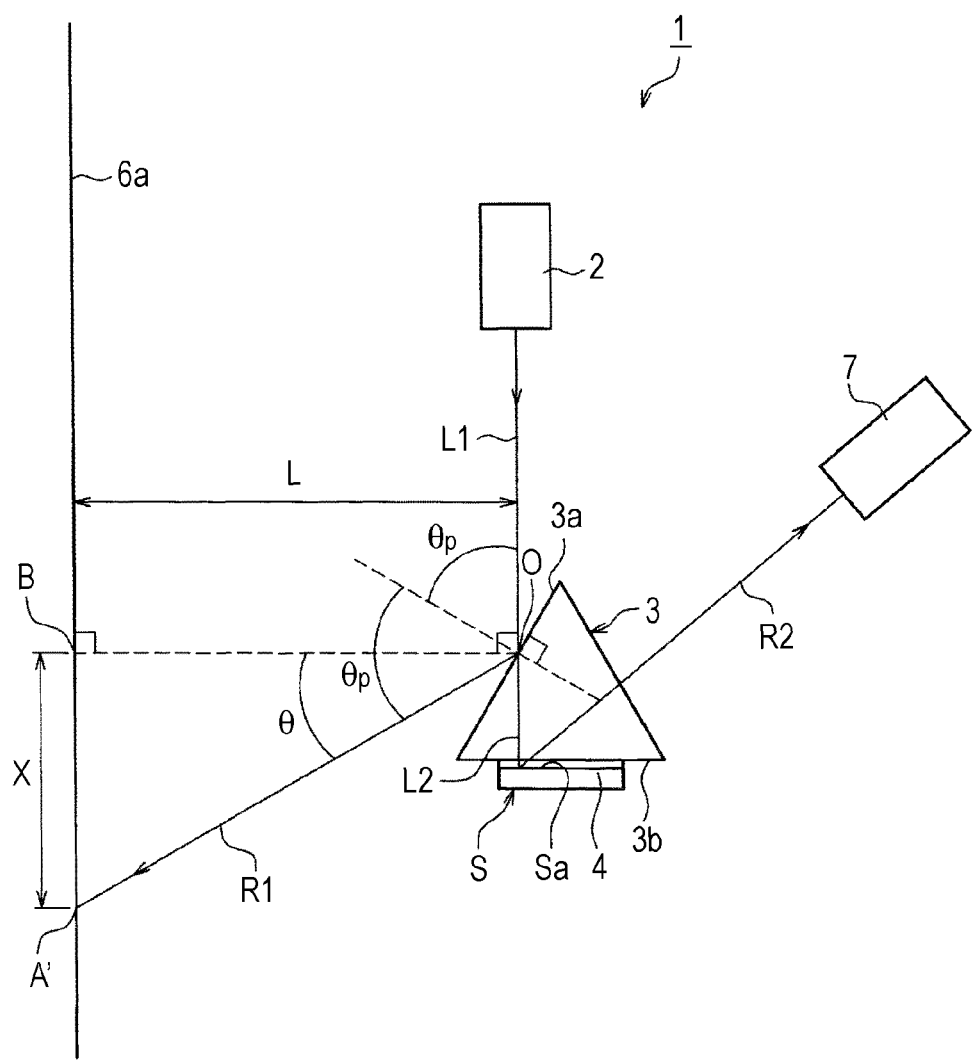
FIG. 4 illustrates another specific example of a refractive index calculating method carried out by the refractive index measuring device.
Figure 5:
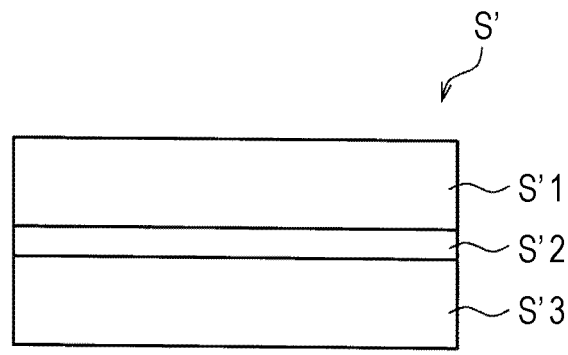
FIGS. 5(a) and 5(b) illustrate solid samples having a multilayer structure.
Figure 5:
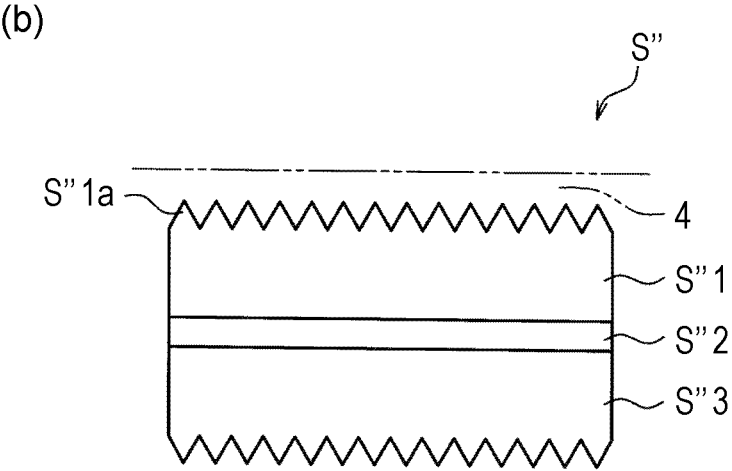
Figure 6:
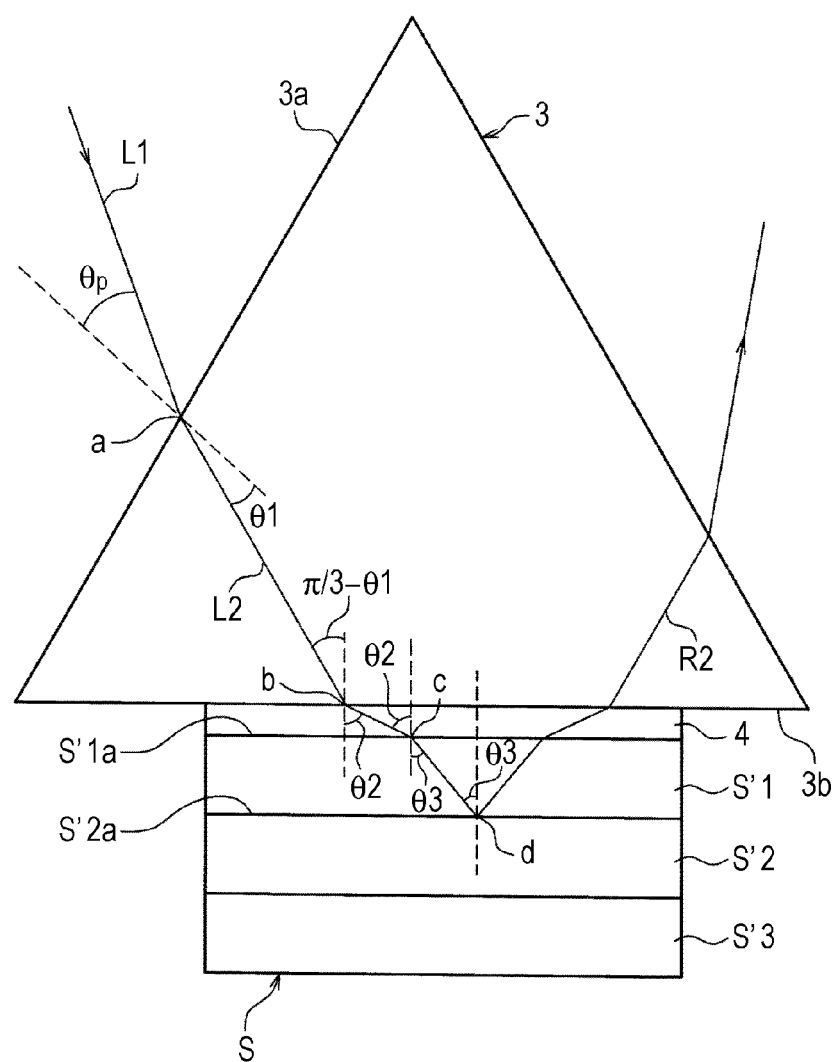
FIG. 6 illustrates a specific example of a refractive index calculating method carried out by the refractive index measuring device in the case where a solid sample has a multilayer structure.

FIG. 2 illustrates a specific example of a refractive index calculating method carried out by the refractive index measuring device. FIG. 3 illustrates a specific example of a refractive index calculating method carried out by the refractive index measuring device in the case where the solid sample has a single-layer structure. FIG. 4 illustrates another specific example of a refractive index calculating method carried out by the refractive index measuring device. FIGS. 5(a) and 5(b) illustrate solid samples having a multilayer structure. FIG. 6 illustrates a specific example of a refractive index calculating method carried out by the refractive index measuring device in the case where the solid sample has a multilayer structure.

First, a case in which the refractive index of the solid sample S having a single-layer structure is determined will be described in detail with reference to FIGS. 2 to 4.

Referring to FIG. 2, when it is determined that the intensity of the second reflected light R2 has become lower than the predetermined value, the distance L between the center of rotation O and the orthogonal position B is known. In addition, the distance X between the orthogonal position B and the position A of the first reflected light R1 on the light receiving surface 6a can be determined by reading the scale marks provided on the light receiving surface 6a. Therefore, an angle θ can be determined from the following Equation (1).

$$\theta = \arctan(X/L) \quad (1)$$

An incident angle θp of the incident light L1 from the light source 2 on the prism 3 can be determined from the following Equation (2).

$$\theta p = \pi/4 - (1/2)\arctan(X/L) \quad (2)$$

Referring to FIG. 3, an incident angle θ2 of the light on the solid sample S is determined from a refracting angle θ1 of the light that enters the prism 3. More specifically, as illustrated in FIG. 3, the incident light L1 changes into the light L2 that passes through the prism 3 at point a (that is, at the center of rotation O). The light L2 enters the refractive index liquid 4 from the prism 3 at point b, and is reflected toward the prism 3 as the second reflected light R2 at point c on the interface between the prism 3 and the refractive index liquid 4.

When the refractive index of the prism 3 is n1, since the refractive index of air is 1.0, the following Equation (3) can be derived from the Snell's law with regard to point a.

$$n1 \sin \theta 1 = \sin \theta p \quad (3)$$

When the refractive index of the refractive index liquid 4 is n2, the following Equation (4) can be derived from the Snell's law with regard to point b.

$$n2 \sin \theta 2 = n1 \sin(\pi/3 - \theta 1) \quad (4)$$

Therefore, when the refractive index n1 of the prism 3 and the refractive index n2 of the refractive index liquid 4 are known, the incident angle θ2 of the light on the solid sample S can be calculated from the distance X. In the state illustrated in FIGS. 2 and 3, the incident angle θ2 of the light on the solid sample S is equal to the critical angle θc. When the refractive index of the solid sample S is n, the critical angle θc can be expressed as in the following Equation (5).

$$\theta c = \arcsin(n/n2) \quad (5)$$

In the state illustrated in FIGS. 2 and 3, that is, when it is determined that the intensity of the second reflected light R2 has become lower than the predetermined value, θc is equal to θ2. Therefore, the refractive index n of the solid sample S can be determined from the distance X.

More specifically, assuming that the refractive index n1 of the prism 3 is n1=1.779, the refractive index n2 of the refractive index liquid 4 is n2=1.560, and the above-described distance L is L=300 mm, when the distance X is X=276 mm, θp, θ1, and θ2 can be determined as θp=0.4135 rad, θ1=0.2278 rad, and θ2=0.9850 rad, respectively, from the above-described Equations (2) to (4). In addition, n can be determined as n=1.300 from Equation (5).

Depending on the solid sample S, as illustrated in FIG. 4, there may be a case in which the position A' of the first reflected light R1 on the light receiving surface 6a is below the orthogonal position B in the figure when the incident angle θ2 of the light on the solid sample S is equal to the critical angle θc. In this case, the incident angle θp of the incident light L1 on the prism 3 can be calculated by using the following Equation (6) instead of the above-described Equation (2). Other calculations can be performed by using the above-described Equations (3) to (5).

$$\theta p = \pi/4 + (1/2)\arctan(X/L) \quad (6)$$

In the case where the refractive index n2 of the refractive index liquid 4 is smaller than the refractive index n of the solid sample S, the condition of total reflection cannot be satisfied after the angle reaches an angle at which the refractive index n2 of the refractive index liquid 4, which is smaller than the refractive index n, is detected. In this case, the refractive index n2 of the refractive index liquid 4, which is smaller than the refractive index n, will be detected as the refractive index n of the solid sample S. Since the refractive index n2 of the refractive index liquid 4 is known, in such a case, a correct refractive index n of the solid sample S can be detected by replacing the refractive index liquid 4 with a refractive index liquid having a refractive index greater than the refractive index n of the solid sample S.

Next, the case in which refractive indices of a solid sample S' having a multilayer structure are determined will be described in detail with reference to FIGS. 5 and 6.

As illustrated in FIG. 5(a), the solid sample S' includes three layers S'1, S'2, and S'3 having different refractive indices. In the following description, it is assumed that the refractive index of the layer S'1 is known and the refractive index of the middle layer S'2 is to be determined. In this case, as illustrated in FIG. 6, the solid sample S' is attached to the prism 3 such that the layer S'1 is closely attached to the second surface 3b of the prism 3 with the refractive index liquid 4 interposed therebetween.

Referring to FIG. 6, when it is determined that the intensity of the second reflected light R2 has become lower than the predetermined value, the distance L between the center of rotation O and the orthogonal position B is known. In addition, the distance X between the orthogonal position B and the position A of the first reflected light R1 on the light receiving surface 6a can be determined by reading the scale marks provided on the light receiving surface 6a.

Similar to the case of the solid sample S having a single-layer structure, the incident angle θp of the incident light L1 from the light source 2 on the prism 3 can be determined from the above-described Equation (2). In addition, similar to the case of the solid sample S having a single-layer structure, the incident angle θ2 of the light on the solid sample S' at point c on a surface S'1a of the solid sample S' that faces the refractive index liquid 4 (that is, the interface between the layer S'1 and the refractive index liquid 4) can be determined from the above-described Equations (3) and (4) derived from the Snell's law with regard to points a and b, respectively.

When the refractive index of the layer S'1 is n3, the refractive index of the middle layer S'2 that is to be measured is n, and the incident angle of the light on the middle layer S'2 at point d, at which the second reflected light R2 is generated, on a surface S'2a of the layer S'2 that faces the refractive index liquid 4 (that is, the interface between the layer S'1 and the layer S'2) is θ3, the following Equation (7) can be derived from the Snell's law with regard to point c.

$$n2 \sin θ2 = n3 \sin θ3 \qquad (7)$$

Therefore, when the refractive index n1 of the prism 3, the refractive index n2 of the refractive index liquid 4, and the refractive index n3 of the layer S'1 are known, the incident angle θ3 of the light on the middle layer S'2 can be calculated from the distance X. In the state illustrated in FIG. 6, the incident angle θ3 of the light on the middle layer S'2 is equal to the critical angle θc. When the refractive index of the middle layer S'2 is n, the critical angle θc can be expressed as in the following Equation (8).

$$θc = \arcsin(n/n3) \qquad (8)$$

In the state illustrated in FIG. 6, that is, when it is determined that the intensity of the second reflected light R2 has become lower than the predetermined value, θc is equal to θ3. Therefore, the refractive index n of the middle layer S'2 can be determined from the distance X.

More specifically, assuming that the refractive index n1 of the prism 3 is n1=1.779, the refractive index n2 of the refractive index liquid 4 is n2=1.560, the refractive index n3 of the layer S'1 is n3=1.585, and the above-described distance L is L=300 mm, when the distance X is X=276 mm, θp, θ1, θ2, and θ3 can be determined as θp=0.4135 rad, θ1=0.2278 rad, θ2=0.9850 rad, θ3=0.9617 rad, respectively, from the above-described Equations (2) to (4) and (7). In addition, n can be determined as n=1.300 from Equation (8).

In the case where the refractive index n1 of the prism 3, the refractive index n2 of the refractive index liquid 4, or the refractive index n3 of the layer S'1 is smaller than the refractive index n of the middle layer S'2, the condition of total reflection cannot be satisfied after the angle reaches an angle at which the refractive index n1 of the prism 3, the refractive index n2 of the refractive index liquid 4, or the refractive index n3 of the layer S'1 that is smaller than the refractive index n is detected. In this case, the refractive index n1 of the prism 3, the refractive index n2 of the refractive index liquid 4, or the refractive index n3 of the layer S'1 that is smaller than the refractive index n will be detected as the refractive index n of the middle layer S'2. Since the refractive index n1 of the prism 3, the refractive index n2 of the refractive index liquid 4, and the refractive index n3 of the layer S'1 are known, in such a case, a correct refractive index n of the middle layer S'2 can be detected by replacing the prism 3, the refractive index liquid 4, or the layer S'1 to those having a refractive index greater than the refractive index n of the middle layer S'2.

In the case where the refractive index of the layer S'3 is to be measured, the refractive index of the layer S'3 can be determined by calculating an incident angle of the light on the layer S'3 by using the Snell's law with regard to point d. Alternatively, the refractive index of the layer S'3 may be measured by closely attaching the layer S'3 to the second surface 3b of the prism 3 with the refractive index liquid 4 interposed therebetween.

Referring to FIG. 5(b), in the case where the solid sample S" includes three layers S"1, S"2, and S"3 and the layer S"1 has small projections S"1a, the refractive index of the middle layer S"2 can be accurately determined by using a refractive index liquid having the same refractive index as that of the layer S"1 as the refractive index liquid 4.

The refractive index measuring device 1 according to the present embodiment is preferably calibrated so that the distance L can be more accurately determined. More specifically, the distance L can be more accurately determined by performing a measurement while only the refractive index liquid 4 having a known refractive index is closely attached to the second surface 3b of the prism 3 or while the second surface 3b of the prism 3 is in contact with only air and the refractive index liquid 4 is not closely attached thereto. Accordingly, components, such as the scale 6, of the refractive index measuring device 1 can be appropriately positioned.

In the refractive index measuring device 1 according to the present embodiment having the above-described structure, when the prism 3 is rotationally driven by the rotary table (rotational drive unit) 5 and the intensity of the second reflected light R2 detected by the detector 7 becomes lower than the predetermined value, the refractive index of the solid sample S is measured by using the position A of the first reflected light R1 on the light receiving surface 6a of the scale (light receiving member) 6. Accordingly, unlike the above-described example of the related art, the accuracy of measurement of the refractive index of the solid sample S can be increased by increasing the distance between the prism 3 and the light receiving surface 6a of the scale 6.

In the present embodiment, the light source 2 and the prism 3 are arranged so that the first reflected light R1 is reflected toward the light receiving surface 6a of the scale by the first surface 3a of the prism 3 at the center of rotation O of the prism 3. In addition, in the present embodiment, the refractive index of the solid sample S is measured by using the distance L between the center of rotation O and the orthogonal position B, which is a position where a perpendicular dropped from the center of rotation O to the light receiving surface 6a of the scale 6 reaches the light receiving surface 6a, and the distance X between the orthogonal position B on the light receiving surface 6a and the position A of the first reflected light R1 on the light receiving surface 6a of the scale 6. Accordingly, the refractive index of the solid sample S can be easily determined.

Second Embodiment

Figure 7:
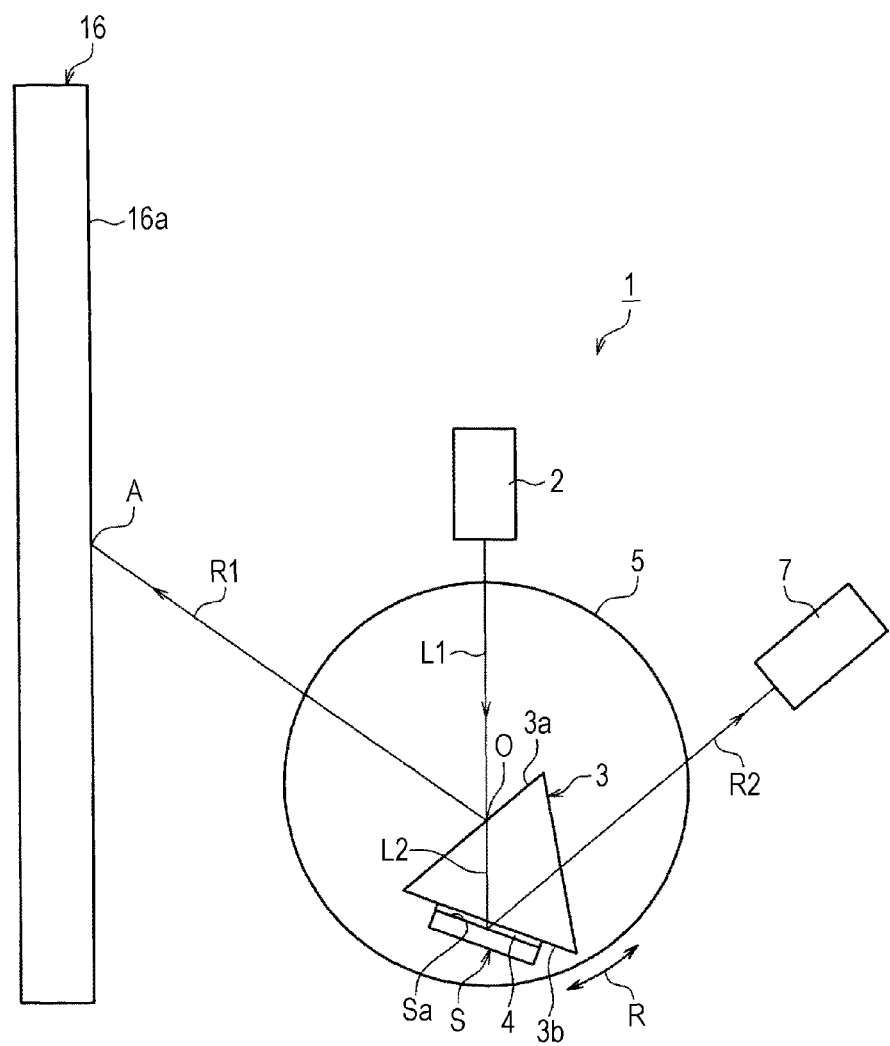
FIG. 7 illustrates the overall structure of a refractive index measuring device according to a second embodiment of the present invention.
Figure 8:
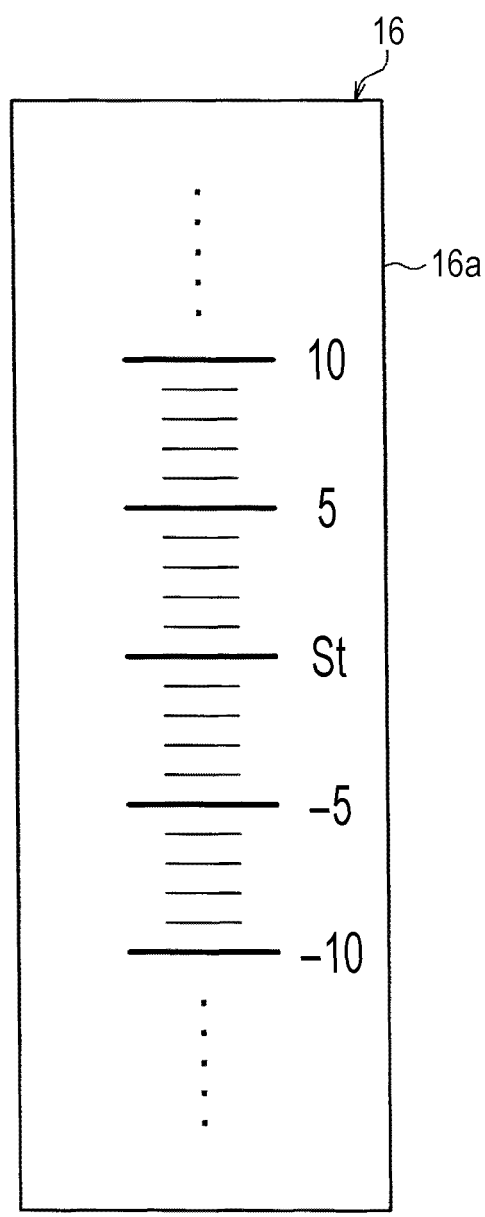
FIG. 8 is a plan view illustrating the structure of a scale illustrated in FIG. 7.

FIG. 7 illustrates the overall structure of a refractive index measuring device according to a second embodiment of the present invention. FIG. 8 is a plan view illustrating the structure of a scale illustrated in FIG. 7. Referring to the figures, the present embodiment mainly differs from the above-described first embodiment in that a scale (light receiving member) having the following structure is used. That is, scale marks are provided on a light receiving surface of the scale, the scale marks including a scale mark indicating a standard position of the first reflected light in the case where the solid sample has a standard refractive index and scale marks which have predetermined intervals therebetween and which indicate displacements from the standard position. Elements similar to those in the above-described first embodiment are denoted by the same reference numerals, and explanations thereof will be omitted to avoid redundancy.

As illustrated in FIG. 7, in a refractive index measuring device 1 according to the present embodiment, incident light L1 from a light source 2 is incident on a prism 3, and is reflected at the center of rotation O of the prism 3 as first reflected light R1. The first reflected light R1 is received by a light receiving surface 16a of a scale (light receiving member) 16. Light L2 that enters the prism 3 at the center of rotation O of the prism 3 is reflected by a surface Sa of a solid sample S that faces a refractive index liquid 4 as second reflected light R2. The second reflected light R2 is received by a detector 7.

As illustrated in FIG. 8, scale marks are provided on the light receiving surface 16a of the scale 16, the scale marks including a scale mark indicating a standard position St of the first reflected light R1 in the case where the solid sample S has a standard refractive index and scale marks which have predetermined intervals therebetween and which indicate displacements from the standard position St. These scale marks are drawn by measuring a refractive index of a material having a known refractive index and determining the position corresponding to the measurement result as the standard position St.

More specifically, a position A of the first reflected light R1 (position at which the first reflected light R1 is received) is determined while only the refractive index liquid 4 having a known refractive index is closely attached to the second surface 3b of the prism 3 or while the second surface 3b is in contact with only air and the refractive index liquid 4 is not bonded thereto. The determined position A is set as the standard position St on the light receiving surface 16a, and scale marks are drawn on the light receiving surface 16a with intervals of, for example, 0.001 in terms of refractive index, as illustrated in FIG. 8.

In the present embodiment, a correlation table showing the correlation between the positions of the scale marks and the values of refractive index is prepared in advance. In the above-described refractive index detecting step, the refractive index of the solid sample S is determined by reading the scale marks on the light receiving surface 16a of the scale 16 and referring to the correlation table. In other words, the refractive index of the solid sample S is determined by determining a displacement from the standard position St and referring to the correlation table.

With the above-described structure, the present embodiment provides advantages and effects similar to those of the above-described first embodiment. In addition, the scale marks are provided on the light receiving surface 6a of the scale (light receiving member) 16 according to the present embodiment, the scale marks including a scale mark indicating the standard position St of the first reflected light R1 in the case where the solid sample S has a standard refractive index and scale marks which have predetermined intervals therebetween and which indicate displacements from the standard position St. Accordingly, in the present embodiment, the refractive index of the solid sample S can be more easily determined.

Third Embodiment

Figure 9:
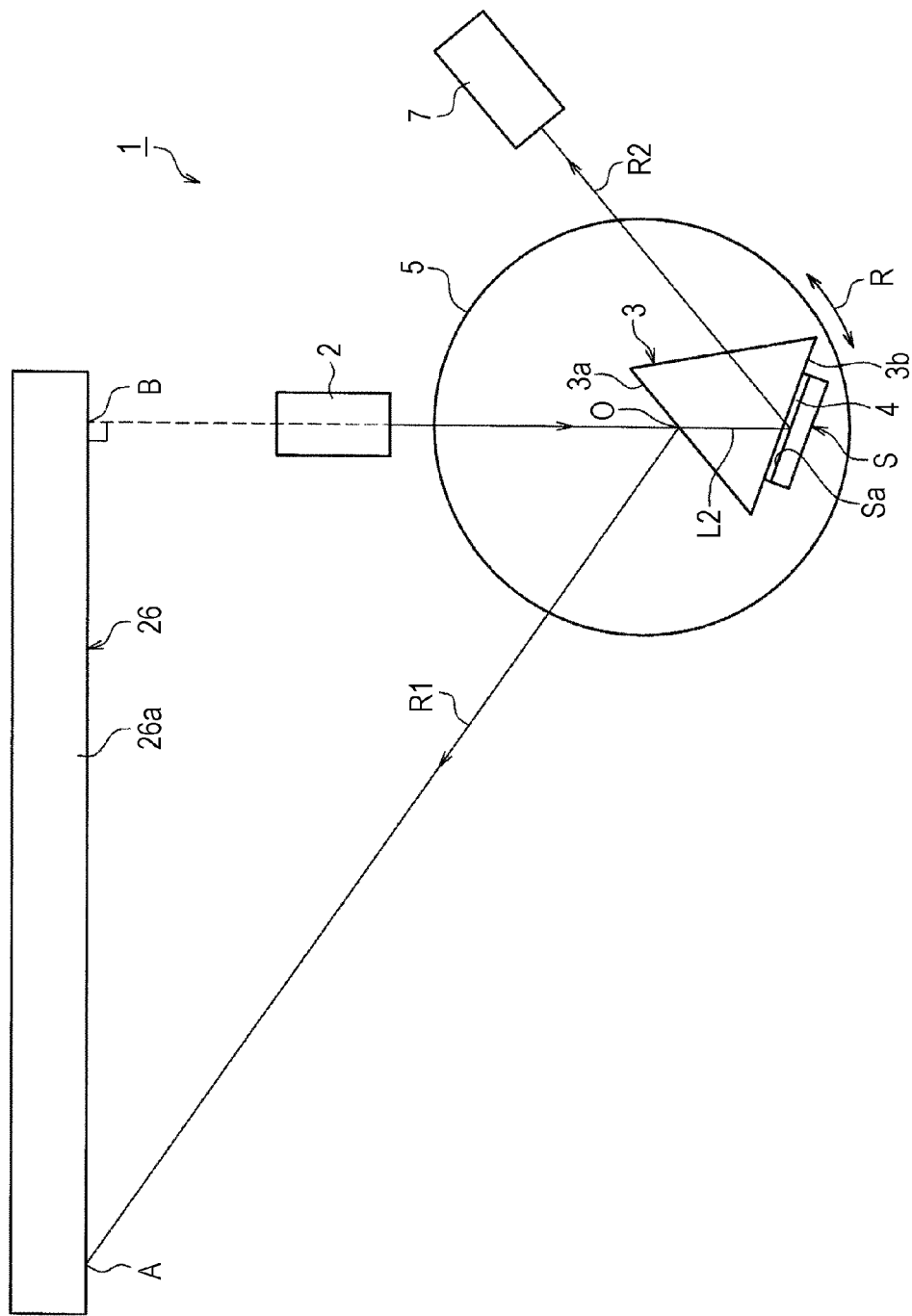
FIG. 9 illustrates the overall structure of a refractive index measuring device according to a third embodiment of the present invention.

FIG. 9 illustrates the overall structure of a refractive index measuring device according to a third embodiment of the present invention. Referring to the figure, the present embodiment mainly differs from the above-described second embodiment in that a light source and a scale (light receiving member) are arranged so that a light receiving surface is orthogonal to incident light that travels from the light source to a prism. Elements similar to those in the above-described second embodiment are denoted by the same reference numerals, and explanations thereof will be omitted to avoid redundancy.

As illustrated in FIG. 9, in a refractive index measuring device 1 according to the present embodiment, a light source 2 and a scale (light receiving member) 26 are arranged so that a light receiving surface 26a is orthogonal to incident light L1 that travels from the light source 2 to a prism 3. In the refractive index measuring device 1 according to the present embodiment, similar to the second embodiment, the incident light L1 from the light source 2 is incident on the prism 3, and is reflected at the center of rotation O of the prism 3 as first reflected light R1. The first reflected light R1 is received by the light receiving surface 26a of the scale 26. Light L2 that enters the prism 3 at the center of rotation O of the prism 3 is reflected by a surface Sa of a solid sample S that faces a refractive index liquid 4 as second reflected light R2. The second reflected light R2 is received by a detector 7.

With the above-described structure, the present embodiment provides advantages and effects similar to those of the above-described second embodiment.

Fourth Embodiment

Figure 10:
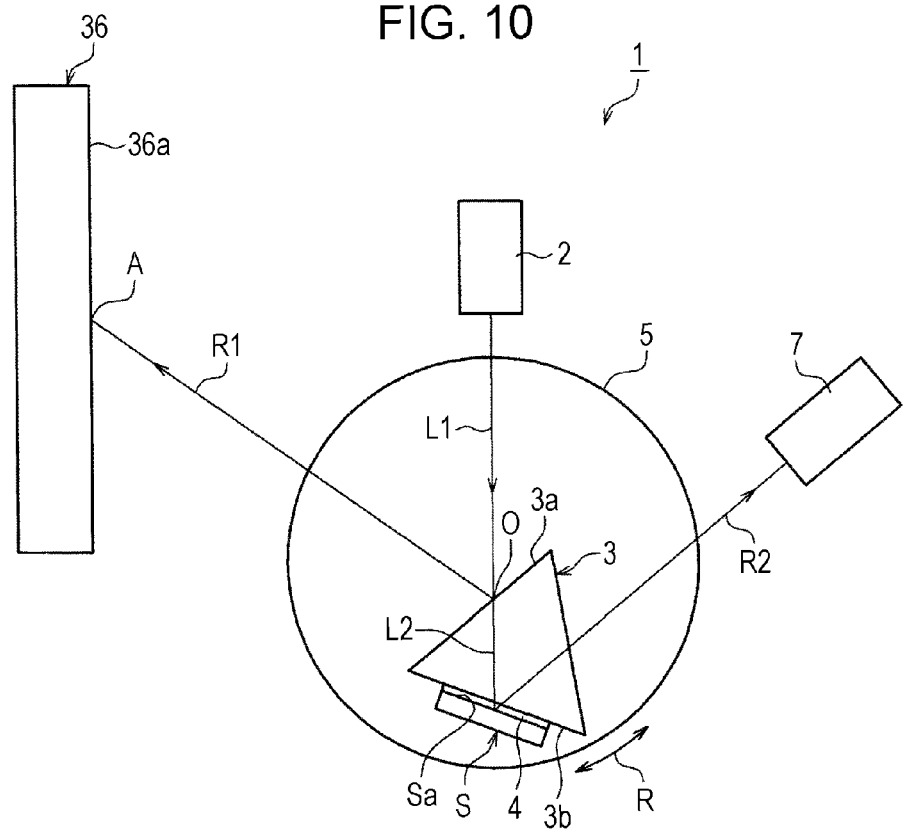
FIG. 10 illustrates the overall structure of a refractive index measuring device according to a fourth embodiment of the present invention.
Figure 11:
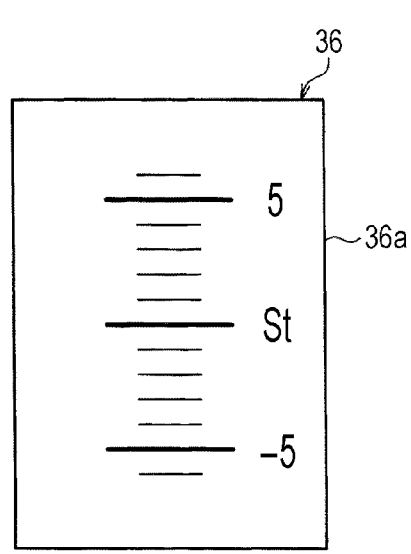
FIG. 11 is a plan view illustrating the structure of a scale illustrated in FIG. 10.

FIG. 10 illustrates the overall structure of a refractive index measuring device according to a fourth embodiment of the present invention. FIG. 11 is a plan view illustrating the structure of a scale illustrated in FIG. 10. Referring to the figures, the present embodiment mainly differs from the above-described second embodiment in that a scale (light receiving member) used in the present embodiment has a light receiving surface on which scale marks that correspond to refractive indices within an allowable refractive index range of the solid sample are provided. Elements similar to those in the above-described second embodiment are denoted by the same reference numerals, and explanations thereof will be omitted to avoid redundancy.

As illustrated in FIG. 10, in a refractive index measuring device 1 according to the present embodiment, incident light L1 from a light source 2 is incident on a prism 3, and is reflected at the center of rotation O of the prism 3 as first reflected light R1. The first reflected light R1 is received by a light receiving surface 36a of a scale (light receiving member) 36. Light L2 that enters the prism 3 at the center of rotation O of the prism 3 is reflected by a surface Sa of a solid sample S that faces a refractive index liquid 4 as second reflected light R2. The second reflected light R2 is received by a detector 7.

As illustrated in FIG. 11, scale marks that correspond to refractive indices within an allowable refractive index range of the solid sample S are provided on the light receiving surface 36a of the scale 36. More specifically, similar to the second embodiment, scale marks are provided on the light receiving surface 36a, the scale marks including a scale mark indicating a standard position St of the first reflected light R1 in the case where the solid sample S has a standard refractive index and scale marks which have predetermined intervals therebetween and which indicate displacements from the standard position St. The scale marks on the light receiving surface 36a of the scale 36 correspond to refractive indices within the allowable refractive index range of the solid sample.

According to the present embodiment, in the above-described refractive index detecting step, the refractive index of the solid sample S is measured by using the scale marks that correspond to the refractive indices within the allowable refractive index range of the solid sample S. More specifically, when the first reflected light R1 is received by the light receiving surface 36a in the refractive index detecting step, the refractive index of the solid sample S is determined on the basis of the position at which the first reflected light R1 is received. In this case, the refractive index of the solid sample S is within the allowable range, and it can be determined that the solid sample S can be used as a product.

When the first reflected light R1 cannot be received by the light receiving surface 36a in the refractive index detecting step, the refractive index of the solid sample S is out of the allowable range and it can be determined that the solid sample S cannot be used as a product.

With the above-described structure, the present embodiment provides advantages and effects similar to those of the above-described second embodiment. In addition, the light receiving surface 36a of the scale (light receiving member) 36 according to the present embodiment has scale marks corresponding to refractive indices within the allowable refractive index range of the solid sample S. Accordingly, in the present embodiment, it can be instantly determined whether or not the solid sample S has an acceptable refractive index and the process of inspecting the solid sample S can be simplified.

The above-described embodiments are merely examples, and are not limitative. The technical scope of the present invention is defined by the claims, and all modifications equivalent to configurations described in the claims are also included in the technical scope of the present invention.

For example, according to the above description, the light source and the prism are arranged so that the first reflected light is reflected toward the light receiving surface of the scale (light receiving member) by the first surface of the prism at the center of rotation of the prism. However, the present invention is not limited to this as long as the light from the light source is incident on the first surface of the prism having a predetermined refractive index.

However, as in the above-described embodiment, the light source and the prism are preferably arranged so that the first reflected light is reflected toward the light receiving surface of the light receiving member by the first surface of the prism at the center of rotation of the prism because the refractive index of the solid sample can be easily calculated in that case. More specifically, when the prism is rotated and it is determined that the intensity of the second reflected light has become lower than the predetermined value, the refractive index of the solid sample can be easily determined by using the distance between the center of rotation and the orthogonal position, which is a position where a perpendicular dropped from the center of rotation to the light receiving surface of the light receiving member reaches the light receiving surface, and the distance between the orthogonal position on the light receiving surface and the position of the first reflected light on the light receiving surface of the light receiving member.

According to the above-described first, second, and fourth embodiments, the light source and the scale (light receiving member) are arranged so that the light receiving surface is parallel to the incident light that travels from the light source to the prism. In addition, according to the above-described third embodiment, the light source and the scale (light receiving member) are arranged so that the light receiving surface is orthogonal to the incident light that travels from the light source to the prism. However, the light source and the light receiving member according to the present invention are not limited as long as they are arranged so that the reflected light reflected by the first surface of the prism can be received by the light receiving surface of the light receiving member.

In addition, according to the above description, a scale (light receiving member) having a flat light receiving surface is used. However, the light receiving member according to the present invention is not limited as long as the light receiving member has a light receiving surface that receives the first reflected light, which is a part of the light from the light source and which is reflected by the first surface of the prism. For example, a light receiving member that is recessed and has a spherical light receiving surface may be used.

In addition, according to the above description, a prism having the shape of a regular triangular prism is used. However, the prism according to the present invention is not limited as long as the prism has a predetermined refractive index and includes a first surface on which light from the light source is incident and a second surface which emits light that has passed through the first surface toward the solid sample. For example, the prism may have the shape of an isosceles triangular prism.

However, the prism preferably has the shape of a regular triangular prism as in the above-described embodiments because, in such a case, the refractive index of the solid sample can be easily determined compared to the case in which prisms having other shapes are used.

INDUSTRIAL APPLICABILITY

The present invention is applicable to a refractive index measuring device and a refractive index measuring method with which the accuracy of measurement of a refractive index of a solid sample can be increased.

REFERENCE SIGNS LIST 1 refractive index measuring device
2 light source
3 prism
3a first surface
3b second surface
4 refractive index liquid
5 rotary table (rotational drive unit)
6a, 16, 26, 36 scale (light receiving member)
6a, 16a, 26a, 36a light receiving surface
7 detector
S, S', S" solid sample
R1 first reflected light
R2 second reflected light

The invention claimed is:
1. A refractive index measuring device for measuring a refractive index of a solid sample, comprising:
a light source;
a prism having a predetermined refractive index and including a first surface on which light from the light source is incident and a second surface which emits light that has passed through the first surface toward the solid sample;

a rotational drive unit that rotationally drives the prism;

a refractive index liquid that has a predetermined refractive index and with which the solid sample is closely attached to the second surface of the prism;

a light receiving member having a light receiving surface that receives first reflected light, which is a part of the light from the light source and which is reflected by the first surface of the prism; and a detector that receives second reflected light, which is a part of the light from the second surface of the prism and which is reflected by a surface of the solid sample that faces the refractive index liquid, and detects an intensity of the received second reflected light, wherein when the prism is rotationally driven by the rotational drive unit and the intensity of the second reflected light detected by the detector becomes lower than a predetermined value, the refractive index of the solid sample is measured by using a position of the first reflected light on the light receiving surface of the light receiving member, the light source and the prism are arranged so that the first reflected light is reflected toward the light receiving surface of the light receiving member by the first surface of the prism at a center of rotation of the prism, and wherein the refractive index of the solid sample is measured by using a distance between the center of rotation and an orthogonal position, which is a position where a perpendicular dropped from the center of rotation to the light receiving surface of the light receiving member reaches the light receiving surface, and a distance between the orthogonal position on the light receiving surface and a position of the first reflected light on the light receiving surface of the light receiving member.

2. The refractive index measuring device according to claim 1, wherein scale marks are provided on the light receiving surface of the light receiving member, the scale marks including a scale mark indicating a standard position of the first reflected light in the case where the solid sample has a standard refractive index and scale marks which have predetermined intervals therebetween and which indicate displacements from the standard position.

3. The refractive index measuring device according to claim 1, wherein the scale marks provided on the light receiving surface of the light receiving member correspond to refractive indices within an allowable refractive index range of the solid sample.

4. The refractive index measuring device according to claim 1, wherein the prism has a shape of a regular triangular prism.

5. A refractive index measuring method for measuring a refractive index of a solid sample, the refractive index measuring method comprising:

a solid-sample attaching step of closely attaching the solid sample to a second surface of a prism with a refractive index liquid having a predetermined refractive index interposed therebetween, the prism having a predetermined refractive index and including a first surface on which light from a light source is incident and the second surface which emits light that has passed through the first surface;

a light incidence step of receiving first reflected light with a light receiving surface of a light receiving member, the first reflected light being reflected by the first surface of the prism when the light from the light source is incident on the first surface, and receiving second reflected light with a detector, the second reflected light being a part of the light from the second surface of the prism and being reflected by a surface of the solid sample that faces the refractive index liquid; and a refractive index detecting step of rotating the prism while the solid sample is attached to the prism, determining whether or not an intensity of the second reflected light detected by the detector is lower than a predetermined value, and detecting the refractive index of the solid sample by using a position of the first reflected light on the light receiving surface of the light receiving member when it is determined that the intensity has become lower than the predetermined value, wherein, in the light incidence step, the light from the light source is incident on the first surface of the prism so that the first reflected light is reflected toward the light receiving surface of the light receiving member by the first surface of the prism at a center of rotation of the prism, and wherein, in the refractive index detecting step, the refractive index of the solid sample is measured by using a distance between the center of rotation and an orthogonal position, which is a position where a perpendicular dropped from the center of rotation to the light receiving surface of the light receiving member reaches the light receiving surface, and a distance between the orthogonal position on the light receiving surface and a position of the first reflected light on the light receiving surface of the light receiving member.

6. The refractive index measuring method according to claim 5, wherein, in the refractive index detecting step, the refractive index of the solid sample is measured by using scale marks provided on the light receiving surface of the light receiving member.

7. The refractive index measuring method according to claim 6, wherein, in the refractive index detecting step, the scale marks used to measure the refractive index of the solid sample correspond to refractive indices within an allowable refractive index range of the solid sample.

* * * * *